United States Patent [19]

Nakajima et al.

[11] Patent Number: 5,008,455

[45] Date of Patent: Apr. 16, 1991

[54] METHOD FOR THE PRODUCTION OF HYDROXYLAMINE DERIVATIVES

[75] Inventors: Masashi Nakajima, Takaoka; Nobuo Tomita, Tonami; Kenji Suzaki, Takaoka; Akira Kaneko, Takaoka; Mikio Sawaki, Takaoka, all of Japan

[73] Assignee: Nippon Soda Co., Ltd., Tokyo, Japan

[21] Appl. No.: 445,155

[22] Filed: Dec. 6, 1989

Related U.S. Application Data

[63] Continuation of Ser. No. 897,208, Aug. 18, 1986, abandoned.

[51] Int. Cl.$^5$ .......................................... C07C 239/20
[52] U.S. Cl. ................................. 564/300; 564/112; 564/113; 564/301; 562/621; 560/312
[58] Field of Search ............... 564/300, 301, 112, 113; 560/312; 562/621

[56] References Cited

U.S. PATENT DOCUMENTS

| | | | |
|---|---|---|---|
| 3,184,510 | 5/1965 | Levy | 564/300 |
| 3,541,106 | 11/1970 | Krenzer et al. | 564/300 X |
| 3,957,823 | 5/1976 | Seebach et al. | 564/113 X |
| 4,675,445 | 6/1987 | Davis et al. | 564/112 X |

OTHER PUBLICATIONS

Wagner, "Synthetic Organic Chemistry", pp. 569 and 576–677 (1953).
Millar et al., "Sidgwicks Organic Chemistry of Nitrogen", 3rd Ed., pp. 333–334 (1966).

*Primary Examiner*—Richard L. Raymond
*Attorney, Agent, or Firm*—George B. Oujevolk

[57] ABSTRACT

There is provided a method for the production of hydroxylamine derivatives or the salt thereof in which a salt of hydroxamic acid is reacted with an alkylating agent such as diethyl sulfate to form an ester of hydroxamic acid, which is reacted with mineral acid in an aqueous solution of lower alcohol so as to prepare hydroxylamine derivatives or the salt thereof. In this process, the incorporation of an oxidizing agent or aldehydes in the reaction system will significantly reduce the content of nitrosoamines in the resulting solution of hydroxylamine derivatives or the salt thereof. Therefore, the resulting hydroxylamine derivatives obtained with a lesser content of harmful compound will be useful as an intermediate for the production of drugs and pesticides.

12 Claims, No Drawings

METHOD FOR THE PRODUCTION OF HYDROXYLAMINE DERIVATIVES

This application is a continuation of application Ser. No. 06/897,208, filed Aug. 18, 1986, now abandoned.

FIELD OF THE INVENTION

The present invention relates to a method for the production of hydroxylamine derivatives having the general chemical formula (I); $NH_2OR^1$ wherein $R^1$ is an alkyl group which may have substituent(s), an alkenyl group which may have substituent(s), an alkynyl group, an aryl group which may have substituent(s) or an aralkyl group which may have substituent(s) or the salt thereof, which is an important compound as an intermediate for the production of the agricultural and pharmaceutical chemicals.

DESCRIPTION OF THE PRIOR ART

There is known the general process for the preparation of hydroxylamine derivatives of the general chemical formula (I) in West German Pat. No. 1149364 (1963), which is outlined in the following formulae;

$$NaNO_2 + NaOH + 2 SO_2 \longrightarrow$$

$$HON(SO_3Na)_2 \xrightarrow{(RO)_2SO_2 \text{ or } R^1X, NaOH}$$

$$RON(SO_3Na)_2 \xrightarrow{HCl, H_2O} RONH_2HCl$$

However, this process would result in a lower yield of the desired product. In addition, the conventional method for the production of $NH_2OR$ by the hydrolysis of the ester of hydroxamic acid is disclosed in J. Chem. Soc. 226–229 (1930) in which an allyl ester of benzohydroxamic acid is reacted in an aqueous solution with hydrochloric acid to produce hydrochloride of allyloxyamine as represented in the following formulae;

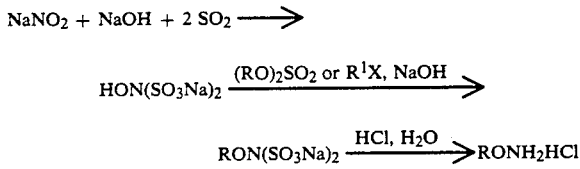

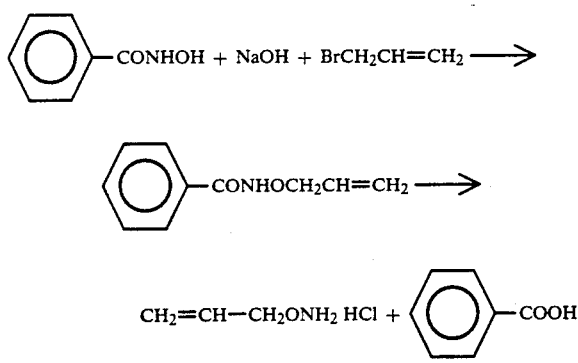

This process would be disadvantageous in that by-product; benzoic acid is formed as a solid substance, and must be removed from the product, which may increase the cost of the process and further in that benzoic acid by itself is costly as compared with the acetate ester.

The process of preparation of $NH_2OR$ from an ester of hydroxamic acid is disclosed in Japanese Tokkyo Koho JP 8229459 in which perchloric acid is used, but this process is disadvantageous in that ethers must be used as solvent, and in that R is limited to di-nitrophenol group or tri-nitrophenol group.

SUMMARY OF THE INVENTION

The inventors of this application have searched the resolution of the above disadvantages, and found an industrially advantageous process with high yield. The inventive process can be represented by the following formulae;

$$R^2COOR^3 + H_2NOH \xrightarrow{M(OH)_n}$$

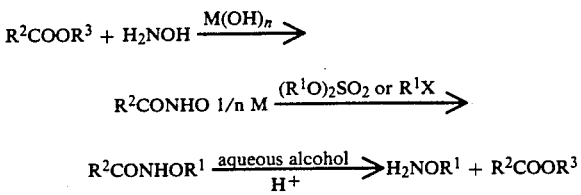

$$R^2CONHOR^1 \xrightarrow[H^+]{\text{aqueous alcohol}} H_2NOR^1 + R^2COOR^3$$

In this process, the inexpensive raw material can be used, and the yield of $R^2CONHOR^1$ can be significantly improved. Further, in the process of this invention, the product; hydroxylamine derivatives can be obtained by the hydrolysis in an aqueous solution of $R^3OH$ by using mineral acid, and then, the by-product $R^2COOH$ can be recovered in the form of $R^2COOR^3$ with high yield and can be recycled into the process of this invention for the preparation of the hydroxylamine derivatives.

It is an object of the invention to provide a new process for the preparation of hydroxylamine derivatives or the salt thereof.

It is another object of the invention to provide a low cost process for the preparation of hydroxylamine derivatives with higher yield.

It is a further object of the invention to provide a process for the preparation of the hydroxylamine derivatives which contains hardly any of the undesired by-product; nitrosoamine compound.

The foregoing and other objects of the invention will become more apparent from the following detailed description.

DETAILED DESCRIPTION OF PREFERRED EMBODIMENTS

In accordance with the present invention, the hydroxylamine derivatives or the salt thereof can be prepared by the following reactions.

The ester of carboxylic acid having the following general chemical formula: $R^2COOR^3$ wherein $R^2$ and $R^3$ are lower alkyl group is reacted with hydroxylamine to form a salt of hydroxamic acid having the general chemical formula; $R^2CONHO$ $1/n$ $M$ wherein $R^2$ is the same as above defined, M is an alkali metal or alkali earth metal, and n is the valency of M, with which the compound having the general chemical formula; $(R^1O)_2SO_2$ or $R^1X$ wherein $R^1$ is an alkyl group which may have substituent(s), an alkenyl group which may have substituent(s), an alkynyl group, aryl group which may have substituent(s) or an aralkyl group which may have substituent(s), X is a nucleophilic reactive group, are reacted to form an ester of hydroxamic acid having the general chemical formula; $R^2CONHOR^1$ wherein $R^1$ and $R^2$ are as same as above defined, with which a mineral acid is reacted in an aqueous solution of alcohol of the chemical formula; $R^3OH$ wherein $R^3$ is a lower alkyl group, to produce hydroxylamine derivatives having the general chemical formula; $NH_2OR^1$ wherein $R^1$ is as same as above defined, or the salt thereof.

The process of this invention can be represented by the following formulaes;

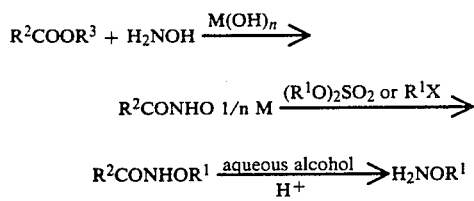

The carboxylic acid obtained from the final step can be recovered not in form of the acid, but in form of the ester; $R^2COOR^3$ with high yield so that the ester can be recycled in the process of this invention for the preparation of hydroxylamine derivatives or the salt thereof.

In accordance with the present invention, the compound of $R^1X$ may include an alkyl halide such as ethyl bromide, n-propyl bromide, iso-propyl bromide, n-butyl bromide, iso-butyl bromide, tert-butyl bromide; an alkenyl halide such as allyl chloride, allyl bromide, 1-propenyl chloride, 1-propenyl bromide, crotyl chloride, 3-butenyl chloride; an alkynyl halide such as propargyl chloride, propargyl bromide, 1-propynyl chloride, 1-propynyl bromide; a benzyl halide such as benzyl chloride, benzyl bromide, o-nitrobenzyl chloride, m-nitrobenzyl chloride, p-nitrobenzyl chloride, 3,5-dinitro benzyl chloride, o-chlorobenzyl chloride, m-chlorobenzyl chloride, p-chlorobenzyl chloride, o-methylbenzyl chloride, m-methylbenzyl chloride, p-methylbenzyl chloride; chlorobenzene such as 2,4-dinitro chlorobenzene, 2,4,6-trinitrochlorobenzene; and an ester of p-toluene sulfonic acid.

When 2-bromoethyl phenyl ether or 1,3-dichloro-2-propene is used, $R^1$ can be 2-phenoxyl ethyl or 3-chloro-2-propenyl group.

Further, in accordance with the present invention, it is not necessary to use dangerous ether, and further, the precipitation of crystals does not occur during the reaction period. In addition, the removal of any by-product and solvent after the completion of the reaction is relatively easy. Therefore, the process of this invention can be said to be industrially worthy and can provide an extremely valuable method for the preparation of hydroxylamine derivatives or the salt thereof.

On the other hand, the solution of the hydroxylamine derivatives prepared by the conventional method is found to involve other technical problem(s) to be solved. That is, for example, undesired impurity; nitrosoamines of the general chemical formula; $(R^1)_2NNO$ is indispensably contained in the amount of 10 to several tens ppm. in the 50% aqueous solution of hydroxylamine derivative prepared by the method disclosed in West German Pat. No. 1149364 (1963) which has a lower yield. Now, the present invention as described can provide a higher yield of the hydroxylamine derivatives, and in addition, can reduce the content of nitrosoamines in the 50% aqueous solution of hydroxylamine derivatives to 2 to 4 ppm.

Further, the inventors of the present invention have been researching the process of the preparation of hydroxylamine derivatives with extremely low content of nitrosoamines and discovered it.

Also, the method hereinafter described comprises two steps as follows:

THE FIRST STEP

The salt of hydroxamic acid represented by the general chemical formula(II); $R^2CONHO$ $1/n$ M wherein $R^2$ is a lower alkyl group, M is an alkali metal or an earth metal, and n is the valency of M, is reacted with a compound represented by the general chemical formula (III); $(R^1O)_2SO_2$ or the general chemical formula (IV); $R^1X$ wherein $R^1$ is an alkyl group which may have substituent(s), an alkenyl group which may have substituent(s), an alkynyl group, aryl group which may have substituent(s), an aralkyl group which may have substituent(s), X is nucleophilic reacting group, thereby to form an ester of hydroxamic acid represented by the general chemical formula (V); $R^2CONHOR^1$ wherein $R^1$ and $R^2$ are as same as above defined.

THE SECOND STEP

The resulting ester of hydroxamic acid (V) is reacted with a mineral acid in an aqueous solution of alcohol having the general chemical formula; $R^3OH$ to form hydroxylamine derivatives representing the general chemical formula (I); $NH_2OR^1$ wherein $R^1$ is the same as above defined.

In the above two-step process for the preparation of hydroxylamine derivatives or the salt thereof, the presence of an oxidizing agent(s) or aldehyde is essential in both reaction steps to reduce the generation of by-products, nitrosoamine compounds. Thus prepared solution of hydroxylamine derivatives was found to contain an extremely small content of nitrosoamines.

The starting material for this two-step process is the salt of hydroxamic acid having the general chemical formula (II), and is not limited to the product obtained from the reaction of the ester of carboxylic acid with hydroxylamine.

The oxidizing agent to be added to the reaction system after the completion of the first step may be potassium permanganate, sodium hypochlorite, cupric sulfate, cupric chloride, and cuprous chloride. After the addition of the oxidizing agent, the agitation of the solution is continued at the temperature of 20° C. to 30° C. for one to several hours. When a cuprous or cupric compound is used as an oxidizing agent, it is advantageous to add the copper compound before the addition of the compound representing the general chemical formula (III) or (IV) in the first step, since it can reduce the amount of the copper compound to be added, and further, can reduce the reaction period of time. In addition, when an aldehyde such as benzaldehyde is used, it is necessary to add the aldehyde before the alkylation reaction in the first step, and then to continue the agitation of the solution at the temperature of 20° C. to 30° C. for 10 to 60 minutes.

The amount of the oxidizing agent or aldehyde to be added is in a range of 0.000005 to 0.01 mole / 1 mole of salt of hydroxamic acid in case of cupric compound(s), and 0.0001 to 0.05 mole / 1 mole of salt of hydroxamic acid in case of the other oxidizing agent(s), and 0.001 to 0.01 mole / 1 mole of salt of hydroxamic acid in case of aldehyde(s).

In the second step, it is preferable to add the cuprous or cupric compound at the stage after lower alcohol ester of carboxylic acid in the aqueous alcohol solution is recovered by the distillation following the addition of mineral acid, or alternatively, at the stage after the succeeding neutralization by the addition of caustic soda. In the latter case, the agitation is continued at a temperature in a range of 20° C. to 70° C. for one to several hours after neutralization. During this procedure, it is preferable to blow air into the solution so as to accelerate oxidation.

When a cuprous or cupric compound is the oxidizing agent added to the solution at the first step, and no isolation is carried out through the first to the second step, there is no need of addition of cupric compound in the second step.

When cupric compound is added in the second step, the amount of cupric compound is in a range of 0.000005 to 0.01 mole per 1 mole of salt of hydroxamic acid.

The inventors have been intensively investigating for the purpose of reducing the content of nitrosoamine compound contained in the hydroxylamine derivatives, and concluded that the nitrosoamine compounds can be produced substantially by the following two routes.

$$NH_2OH + (R^1O)_2SO_2 \text{ [or } R^1X] \longrightarrow \quad (A)$$

$$(R^1)_2NOH \longrightarrow (R^1)_2NNO$$

$$(R^1)_2NH + NH_2OH \xrightarrow{Fe^{3+}} (R^1)_2NNO \quad (B)$$

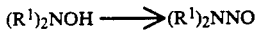
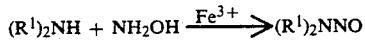

Then, the inventors of the present application have endeavoured to find the method for controlling the production of nitrosoamines from those two routes (A) and (B).

As a conclusion, they found that the effective control method of the nitrosoamines for the route (A) is an addition of aldehyde before the reaction in the first step so as to form oxime thereby to remove $NH_2OH$, and the decomposition by an oxidizing agent of $(R^1)_2NOH$ formed at the first step.

On the other hand, they concluded that the control of nitrosoamines in route (B) should be carried out by the removal of either one of $Fe^{3+}$, $(R^1)_2NH$, or $NH_2OH$.

The removal of $Fe^{3+}$ can be almost completed in the case of a small scale operation such as in a laboratory only by the use of distilled water. In this way, the control of the production of nitrosoamines can be done and the iron ion is prevented from being incorporated in the system. However, the incorporation of $Fe^{3+}$ can not be prevented in mass production such as commercial scale.

Then, the prevention of formation of $(R^1)_2NH$ could be done by the use of less ammonium content in $NH_2OH$ solution, since ammonium hydroxide contained in the solution of $NH_2OH$ used for the production of the compound of the general chemical formula (II) will react with $(R^1O)_2SO_2$ or $R^1X$ to form $(R^1)_2NH$. However, $NH_2OH$ solution with less ammonium content is difficult to produce, and if the $NH_2OH$ solution with higher content of ammonium is employed, it is very difficult to remove $(R^1)_2NH$ from the reaction system.

The control of forming nitrosoamines in route (B) by removing $Fe^{3+}$ or $(R^1)_2NH$ is difficult, and then the inventors have investigated to conclude that the decomposition of $NH_2OH$ remained in the first step is the better and practical measures for this control.

The concrete method is as follows;

The unreacted salt of hydroxamic acid remaining in the first step will produce $NH_2OH$ by the reaction with mineral acid in the second step, and therefore, the removal of $NH_2OH$ only before adding alkylating agent into the first step is not enough. Upon reviewing this method, it is concluded that the decomposition of $NH_2OH$ by the reaction with an oxidizing agent after the neutralization in the second step is also necessary.

When potassium permanganate is employed as an oxidizing agent to be used after the neutralization, the hydroxylamine derivatives having the chemical formula (I) are decomposed. Therefore, the oxidizing agent to be used in the second step should preferably be a cuprous compound or cupric compound. The oxidizing agent used in the first step may be cuprous compound or cupric compound. The copper compound may function as an oxidizing agent in form of cupric compound to be reduced into cuprous compound which can be easily oxidized into the cupric compound by air oxidation, and then, may function again as an oxidizing agent. The amount of the oxidizing compound may be less, and the decomposition of $(R^1)_2NOH$ in the first step and the decomposition of $NH_2OH$ after neutralization in the second step would be almost completed, and there is no influence to the yield of hydroxylamine derivatives to be produced.

The nitrosoamine, $(R^1)_2NNO$ to be formed at the distillation in the route (B) would be incorporated in the fraction of the aqueous solution of hydroxylamine derivatives.

The nitrosoamines from the route (A) would be incorporated in the form of $(R^1)_2NOH$ into the aqueous solution of hydroxylamine derivatives obtained from distillating the reaction mixture of the second step, and then would be converted to $(R^1)_2NNO$ during the storing thereof. When the distilled aqueous solution of hydroxylamine derivatives is used just after the distillation procedure, $(R^1)_2NOH$ contained therein would often be converted to $(R^1)_2NNO$ during the succeeding reaction. In order to review the content of $(R^1)_2NNO$ in the solution in an easy way, the aqueous solution of hydroxylamine derivatives is exposed at the temperature of 50° C. for one week to convert completely $(R^1)_2NOH$ into $(R^1)_2NNO$, and then the measurement on the content of $(R^1)_2NNO$ should be carried out by using gas chromatography.

The following examples illustrate the practice of the invention, but should not be interpreted as a limitation of the invention.

EXAMPLE 1

105.7 G. of ethyl acetate, 92.2 g. of ethanol and 50 g. of water were mixed in 1 l flask, and to the resulting mixture, was added 83.8 g. of hydroxylamine sulfate (purity of 98%) while the mixture was agitated. To the resulting slurry-like solution, were added 659.0 g. of 28% aqueous solution of sodium hydroxide dropwise at the temperature of 20° C. to 30° C. for four hours. Further, the resulting solution was agitated for one more hour at the same temperature. The resulting solution was analyzed by titration curve and the result was found to be 98% in the yield of sodium acetohydroxamate (on the basis of the amount of the starting hydroxylamine sulfate).

To the aqueous solution of sodium acetohydroxamate, were added 165.0 g. of diethyl sulfate dropwise at the temperature of 20° C. to 30° C. for two hours. After the completion of the dropwise addition, the resulting solution was further agitated at the temperature of 20° C. to 30° C. for two hours. The resulting yield of ethyl acetohydroxamate in the aquoues solution was 93% (on the basis of the amount of the starting hydroxylamine sulfate).

Then, to the resulting aqueous solution of ethyl acetohydroxamate were added 230 g. of concentrated hydrochloric acid, and then the resulting solution was heated under reflux for one hour, and then, ethyl acetate was distilled until the distillation temperature of 88° C. for four hours. The distillate was 226 g. The recovered aqueous solution of ethyl acetate and alcohol was analyzed by gas chromatography to conclude that ethyl acetate is 95 g. and ethanol is 86 g. and water is 45 g. and the recovery of ethyl acetate is 90% (on the basis of the amount of the starting ethyl acetate). The resulting residue was further heated to the distillation temperature of 106° C. to distill off ethanol and the other distillate.

The resulting residue was cooled to below 40° C. and then neutralized to pH of 10 by the addition of 28% aqueous solution of sodium hydroxide and then the batch distillation was applied to obtain 110 g. of aqueous solution of ethoxyamine. The concentration thereof was 50% [the yield of ethoxyamine was 90% on the basis of the amount of the starting hydroxylamine sulfate.]

The content of diethylnitrosoamine in the aqueous solution of ethoxyamine was 2.0 ppm by a gas chromatography (Gas chromatography machine; GC-TEA manufactured by Shimadzu Corporation, with the detection limit of 0.03 ppm.). The measured numerical values of content of nitrosoamines appearing hereinafter are based on such measurement procedure.

EXAMPLES 2–11

The similar procedures as described in Example 1 were repeated using $CH_3COOC_2H_5$ as an ester of lower aliphatic acid; $R^2COOR^3$, $C_2H_5OH$ as a lower alcohol; $R^3OH$, ethyl bromide, n-propyl bromide, n-butyl bromide, allyl chloride, propargyl chloride, 2,4-dinitrochlorobenzene, 2,4,6-trinitrochlorobenzene, 4-nitrobenzyl chloride, benzyl chloride, or 4-methylbenzyl chloride as an alkylating agent; $R^1X$ wherein $R^1$ is an alkyl group which may have substituent(s), an alkenyl group which may have substituent(s), an alkynyl group, aryl group which may have substituent(s), an aralkyl group which may have substituent(s), and further, NaOH, KOH or $Ca(OH)_2$ as an alkali metal hydroxide or an alkali earth metal hydroxide; $M(OH)_n$ thereby to form to corresponding hydroxylamine derivatives or the salt thereof. The alkylating agent; $R^1X$ was added dropwise at the temperature of 20° C. to 50° C. and the reaction was carried out at the same temperature for 2 to 7 hours. The result is shown in Table 1.

TABLE 1

| Ex | $R^2COOR^3$ | recovery %, $R^2COOR^3$ | $R^3OH$ | $M(OH)_n$ | $R^1X$ | $R^1ONH_2$ | yield (%) | Note |
|---|---|---|---|---|---|---|---|---|
| 2 | $CH_3COOC_2H_5$ | 89 | $C_2H_5OH$ | NaOH | $CH_2=CH-CH_2Cl$ | $CH_2=CHCH_2ONH_2$ | 90 | |
| 3 | $CH_3COOC_2H_5$ | 85 | $C_2H_5OH$ | NaOH | Ph-$CH_2Cl$ | Ph-$CH_2ONH_2$ | 89 | |
| 4 | $CH_3COOC_2H_5$ | 80 | $C_2H_5OH$ | NaOH | $NO_2$-Ph-$CH_2Cl$ | $NO$-Ph-$CH_2ONH_2$ | 87 | as a hydrochloride |
| 5 | $CH_3COOC_2H_5$ | 83 | $C_2H_5OH$ | NaOH | 2,4-($NO_2$)$_2$-Ph-Cl | 2,4-($NO_2$)$_2$-Ph-$ONH_2$ | 80 | as a hydrochloride |
| 6 | $CH_3COOC_2H_5$ | 85 | $C_2H_5OH$ | NaOH | 2,4,6-($NO_2$)$_3$-Ph-Cl | 2,4,6-($NO_2$)$_3$-Ph-$ONH_2$ | 70 | as a hydrochloride |
| 7 | $CH_3COOC_2H_5$ | 85 | $C_2H_5OH$ | KOH | n-$C_3H_7Br$ | n-$C_3H_7ONH_2$ | 84 | as a hydrochloride |
| 8 | $CH_3COOC_2H_5$ | 83 | $C_2H_5OH$ | KOH | n-$C_4H_9Br$ | n-$C_4H_9ONH_2$ | 70 | as a hydrochloride |
| 9 | $CH_3COOC_2H_5$ | 78 | $C_2H_5OH$ | NaOH | $CH\equiv CCH_2Cl$ | $CH\equiv CCH_2ONH_2$ | 75 | as a hydrochloride |
| 10 | $CH_3COOC_2H_5$ | 82 | $C_2H_5OH$ | NaOH | $CH_3$-Ph-$CH_2Cl$ | $CH_3$-Ph-$CH_2ONH_2$ | 72 | |
| 11 | $CH_3COOC_2H_5$ | 80 | $C_2H_5OH$ | $Ca(OH)_2$ | $C_2H_5Br$ | $C_2H_5ONH_2$ | 77 | |

EXAMPLE 12

To the aqueous solution of sodium acetohydroxamate as similarly prepared in Example 1, were added 1.2 g. of 1% aqueous solution of $CuSO_4$, [0.0075 mole % on the basis of the amount of the starting hydroxylamine sulfate] and then, 165.0 g. of diethyl sulfate were added dropwise at a temperature of 20° C. to 30° C. for two hours. After the completion of the dropwise addition, the resulting solution was further agitated at the temperature of 30° C. for two hours. The yield of ethyl acetohydroxamate in the aqueous solution was 93% (on the basis of the amount of the starting hydroxylamine sulfate).

To the resulting aqueous solution of ethyl acetohydroxamate were added 230 g. of concentrated hydrochloric acid and then heated under reflux for one hour, and then, ethyl acetate was distilled off for four hours until the distillation temperature of 88° C. The distillate was 235 g. The recovered aqueous solution of ethyl acetate and alcohol was analyzed by gas chromatography to conclude that the solution contained 97 g. of ethyl acetate, 89 g. of ethanol, and 49 g. of water, and the recovery of ethyl acetate was 92% (on the basis of the amount of the starting ethyl acetate). Further, the residual solution was heated for two hours to the distillation temperature of 106° C. to distill off ethanol and the other distillate.

The residual solution was cooled below 40° C. and then was neutralized to pH of 10 by the addition of 28% aqueous solution of sodium hydroxide and then the batch distillation was applied to obtain 110 g. of aqueous solution of ethoxyamine. The concentration of ethoxyamine in the solution was 50% [the yield of ethoxyamine was 90% on the basis of the amount of the starting hydroxylamine sulfate].

The content of diethylnitrosoamine in the distilled aqueous solution of ethoxyamine was below 0.03 ppm.

EXAMPLE 13

To the aqueous solution of sodium acetohydroxamate as similarly prepared in Example 1, were added 165.0 g. of diethyl sulfate dropwise at the temperature of 20° C. to 30° C. for two hours. After the completion of the dropwise addition of diethyl sulfate, the solution was further agitated at the temperature of 30° C. for two hours, and then 3.2 g. of 1% aqueous solution of potassium permanganate [corresponding to 0.02 mole % on the basis of the amount of the starting hydroxylamine sulfate] was added and further the resulting solution was agitated at the same temperature for two hours. Then, the procedure as in Example 1 was carried out to obtain 110 g. of aqueous solution of ethoxyamine. The concentration of the solution was 49% [corresponding to 88% of the yield on the basis of the amount of the starting hydroxylamine sulfate].

The content of diethylnitrosoamine in the residual aqueous solution of ethoxyamine was below 0.03 ppm.

EXAMPLE 14

To the aqueous solution of sodium acetohydroxamate as similarly prepared in Example 1, were added 0.53 g. of benzaldehyde (corresponding to 0.5 mole % on the basis of the amount of the starting hydroxylamine sulfate) and then the resulting solution was agitated at the temperature of 20° C. to 30° C. for 30 minutes.

Then, 165.0 g. of diethyl sulfate were added dropwise to the solution at a temperature of 20° C. to 30° C. for two hours. The resulting solution was executed by the same procedure as in Example 1 to obtain 110 g. of aqueous solution of ethoxyamine. The concentration of ethoxyamine in the solution was 50% [corresponding to 90% of the yield on the basis of the amount of the starting hydroxylamine sulfate], and the content of diethylnitrosoamine was found to be 0.08 ppm.

EXAMPLE 15

1723 Kg. of ethyl acetate, 1387 kg. of ethanol, 1260 kg. of hydroxylamine sulfate( purity of 98% ) and 752 kg. of water were put in a reaction vessel of 11 m³ in volume, and to the resulting solution, were 5015 kg. of 28% aqueous solution of sodium hydroxide added dropwise at a temperature of 20° C. to 40° C. for four hours. The resulting solution was further agitated at the same temperature for additional 30 minutes.

Then, to the resulting aqueous solution of sodium acetohydroxamate, were added 17 kg. of 1% aqueous solution of cupric sulfate, and then, 2482 kg. of diethyl sulfate were added dropwise at a temperature of 20° C. to 30° C. for two hours. After the completion of the dropwise addition, the resulting solution was further agitated at the same temperature for four hours.

Then, the resulting aqueous solution of ethyl acetohydroxamate was poured into a reaction vessel of 15 m³ in volume, and 3372 kg. of 35% hydrochloric acid was added and then, the resulting solution was heated under reflux for one hour.

Then, the resulting mixture of ethyl acetate, ethanol, water and the other component(s) was distilled for four hours until the distillation temperature reached to the temperature of 88° C. The resulting distillate was adjusted in pH and then was used to prepare sodium acetohydroxamate, or the starting material.

The residual solution was heated for 8 hours until the temperature of the solution reached to 114° C., the residual ethanol and the other substance were distilled out.

Then, the residual solution was cooled to 50° C. and was neutralized in a neutralization vessel of 4 m³ in volume to pH of 10 to 10.5 by the addition of 28% aqueous solution of sodium hydroxide, and during the period of the neutralization, air was blown in the solution to oxidize and decompose hydroxylamine and the other component, ( the average residence time was four hours ). Such continuous distillation resulted in 1592 kg. of aqueous solution of ethoxyamine. The resulting concentration of ethoxyamine in the solution was 53% (corresponding to 92% of the yield on the basis of the amount of the starting hydroxylamine sulfate). The content of diethylnitrosoamine was found to be 0.03 ppm.

As supported in each of the above Examples, the inventive process can provide significantly higher yield of hydroxylamine derivatives, and furthermore, can significantly reduce the content of nitrosoamines in the resulting solution of hydroxylamine derivatives to the value of which was negligible.

What is claimed is:

1. A process for the production of hydroxylamine derivatives having the general chemical formula:

$$NH_2OR^1 \qquad (I)$$

comprising:

(a) reacting an ester of carboxylic acid having the general chemical formula:

$$R^2COOR^3, \qquad (II)$$

wherein $R^2$ is a lower alkyl, with an hydroxylamine having the formula:

$$HONH_2 \qquad (III)$$

to form a salt of hydroxamic acid having the general chemical formula:

$$R^2CONHO\ 1/n\ M; \qquad (IV)$$

(b) reacting the resulting salt of hydroxamic acid having the formula (IV) with a compound having the general formula:

$$(R^1O)_2SO_2\ or\ R^1X \qquad (V)$$

to form an ester of hydroxamic acid having the general formula:

$$R^2CONHOR^1; \qquad (VI)$$

(c) reacting the ester of hydroxamic acid (VI) with a mineral acid in an aqueous solution of an alcohol having the formula:

$$R^3OH \qquad (VII)$$

to produce hydroxylamine derivatives having the general formula (I) and an ester of carboxylic acid having the general chemical formula (II); and (d) introducing the ester of carboxylic acid having the general chemical formula (II) into the reaction of step (a), wherein said process is carried out in aqueous solution;

$R^1$ is selected from the group consisting of an alkyl group, a substituted alkyl group, an alkenyl group, a substituted alkenyl group, an alkynyl group, a substituted alkynyl group, an aryl group, a substituted aryl group, an aralkyl group, a substituted aralkyl group, and salts thereof;

$R^2$ and $R^3$ are selected from the group consisting of lower alkyl groups;

M is an alkali metal or an alkali earth metal;

n is the valency of M;, and

X is a nucleophilic reacting group.

2. A process for the production of hydroxylamine derivatives having the general chemical formula:

$$NH_2OR^1 \qquad (I)$$

comprising:

(a) reacting an ester of carboxylic acid having the general chemical formula:

$$R^2COOR^3, \qquad (II)$$

wherein $R^2$ is a lower alkyl, with an hydroxylamine having the formula:

$$HONH_2 \qquad (III)$$

to form a salt of hydroxamic acid having the general chemical formula:

$$R^2CONHO \; 1/n \; M; \qquad (IV)$$

(b) reacting the resulting salt of hydroxamic acid having the formula (IV) with a compound having the general formula:

$$(R^1O)_2SO_2 \text{ or } R^1X \qquad (V)$$

to form an ester of hydroxamic acid having the general formula:

$$R^2CONHOR^1; \qquad (VI)$$

(c) reacting the ester of hydroxamic acid (VI) with a mineral acid in an aqueous solution of an alcohol having the formula:

$$R^3OH \qquad (VII)$$

to produce hydroxylamine derivatives having the general formula (I) and an ester of carboxylic acid having the general chemical formula (II); and (d) introducing the ester of carboxylic acid having the general chemical formula (II) into the reaction of step (a), wherein said process is carried out in aqueous solution;

at least one agent selected from the group consisting of oxidizing agents that are effective in inhibiting the formation of nitrosamines and aldehydes that are effective in inhibiting the formation of nitrosamines is added to the reaction after step (a) or after step (b) at a concentration sufficient to substantially inhibit the formation of nitrosamines;

$R^1$ is selected from the group consisting of an alkyl group, a substituted alkyl group, an alkenyl group, a substituted alkenyl group, an alkynyl group, a substituted alkynyl group, an aryl group, a substituted aryl group, an aralkyl group, a substituted aralkyl group, and salts thereof;

$R^2$ and $R^3$ are selected from the group consisting of lower alkyl groups;

M is an alkali metal or an alkali earth metal;

n is the valency of M;, and

X is a nucleophilic reacting group.

3. The process of claim 2, wherein said oxidizing agents are cuprous compounds and cupric compounds.

4. The process of claim 3, wherein the concentration of said cuprous and cupric compounds is in the range of $5 \times 10^{-6}$ to $1 \times 10^{-2}$ moles/mole of said salt of hydroxamic acid of formula (IV).

5. The process of claim 2, wherein said aldehydes are added to the reaction after step (a) at a concentration in the range of $1 \times 10^{-4}$ to $1 \times 10^{-2}$ moles/mole of salt of said hydroxamic acid.

6. The process of claim 2, wherein said agents are selected from the group consisting of potassium permanganate, sodium hypochlorite and benzaldehyde.

7. The process of claim 3, wherein said agents are selected from the group consisting of cupric sulfate, cupric chloride and cuprous chloride.

8. The process of claim 2, wherein said agent is added to said process at step (b).

9. The process of claim 8, wherein the concentration of said agent is in the range of $5 \times 10^{-6}$ to $1 \times 10^{-2}$ mole/mole of said salt of hydroxamic acid of formula (IV).

10. The process of claim 3, wherein said cuprous and cupric compounds are added to said process at step (c).

11. The process of claim 10, wherein the cuprous and cupric compounds are selected from the group consisting of cupric sulfate, cupric chloride and cuprous chloride.

12. The process of claim 11, wherein the concentration of said cuprous and cupric compounds is in the range of $5 \times 10^{-6}$ to $1 \times 10^{-2}$ mole/mole of said salt of hydroxamic acid of formula (IV).

* * * * *